(12) United States Patent
Daines et al.

(10) Patent No.: US 6,486,192 B1
(45) Date of Patent: Nov. 26, 2002

(54) INDOLE COMPOUNDS USEFUL FOR TREATING BACTERIAL INFECTIONS

(75) Inventors: Robert A. Daines, Lansdale, PA (US); Pamela A. Chambers, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/980,164

(22) PCT Filed: Jun. 22, 2000

(86) PCT No.: PCT/US00/17263

§ 371 (c)(1),
(2), (4) Date: Nov. 28, 2001

(87) PCT Pub. No.: WO00/78310

PCT Pub. Date: Dec. 28, 2000

Related U.S. Application Data

(60) Provisional application No. 60/140,557, filed on Jun. 23, 1999.

(51) Int. Cl.$^7$ ................................................ A61K 31/40
(52) U.S. Cl. ........................................ 514/418; 514/414
(58) Field of Search ................................. 514/418, 414

(56) References Cited

U.S. PATENT DOCUMENTS 5,482,960 A    1/1996   Berryman et al.

*Primary Examiner*—William R. A. Jarvis
(74) *Attorney, Agent, or Firm*—Soma G. Simon; Mary E. McCarthy; Charles M. Kinzig

(57) ABSTRACT

This invention relates to the use of certain indole compounds, which are active as inhibitors of the fatty acid synthase FabH, for the treatment of bacterial infections.

3 Claims, No Drawings

INDOLE COMPOUNDS USEFUL FOR TREATING BACTERIAL INFECTIONS

This is a 371 of PCT/US00/17263, filed Jun. 22, 2000, which claims priority to provisional application No. 60/140, 557, filed Jun. 23, 1999.

FIELD OF THE INVENTION

This invention relates to the use of compounds as inhibitors of the fatty acid synthase FabH.

BACKGROUND OF THE INVENTION

The pathway for the biosynthesis of saturated fatty acids is very similar in prokaryotes and eukaryotes. However, although the chemical reactions may not vary, the organization of the biosynthetic apparatus is very different. Vertebrates and yeasts possess type I fatty acid syntheses (FASs) in which all of the enzymatic activities are encoded on one or two polypeptide chains, respectively. The acyl carrier protein (ACP) is an integral part of the complex. In contrast, in most bacterial and plant FASs (type II) each of the reactions are catalyzed by distinct monofunctional enzymes and the ACP is a discrete protein. Mycobacteria are unique in that they possess both type I and II FASs; the former is involved in basic fatty acid biosynthesis whereas the latter is involved in synthesis of complex cell envelope lipids such as mycolic acids. There therefore appears to be considerable potential for selective inhibition of the bacterial systems by broad spectrum antibacterial agents (Jackowski, S. 1992. In Emerging Targets in Antibacterial and Antifungal Chemotherapy. Ed. J. Sutcliffe & N. Georgopapadakou. Chapman & Hall, New York; Jackowski, S. et al. (1989). J. Biol. Chem. 264, 7624–7629.)

The first step in the biosynthetic cycle is the condensation of malonyl-ACP with acetyl-CoA by FabH. In subsequent rounds malonyl-ACP is condensed with the growing-chain acyl-ACP (FabB and FabF, syntheses I and II respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by NADH-dependent enoyl-ACP reductase (FabI). Further rounds of this cycle, adding two carbon atoms per cycle, eventually lead to palmitoyl-ACP whereupon the cycle is stopped largely due to feedback inhibition of FabH and I by palmitoyl-ACP (Heath, et al, (1996), J.Biol.Chem. 271, 1833–1836). Fab H is therefore a major biosynthetic enzyme which is also a key regulatory point in the overall synthetic pathway (Heath, R. J. and Rock, C. O. 1996. J.Biol.Chem. 271, 1833–1836; Heath, R. J. and Rock, C. O. 1996. J.Biol.Chem. 271, 10996–11000).

The antibiotic thiolactomycin has broad-spectrum antibacterial activity both in vivo and in vitro and has been shown to specifically inhibit all three condensing enzymes. It is non-toxic and does not inhibit mammalian FASs (Hayashi, T. et al., 1984. J. Antibiotics 37, 1456–1461; Miyakawa, S. et al., 1982. J. Antibiotics 35, 411–419; Nawata, Y et al., 1989. Acta Cryst. C45, 978–979; Noto, T. et al., 1982. J. Antibiotics 35,401–410; Oishi, H. et al., 1982. J. Antibiotics 35, 391–396. Similarly, cerulenin is a potent inhibitor of FabB & F and is bactericidal but is toxic to eukaryotes because it competes for the fatty-acyl binding site common to both FAS types (D'Agnolo, G. et al., 1973. Biochim. Biophys. Acta. 326, 155–166). Extensive work with these inhibitors has proved that these enzymes are essential for viability. Little work has been carried out in Gram-positive bacteria.

There is an unmet need for developing new classes of antibiotic compounds that are not subject to existing resistance mechanisms. No marketed antibiotics are targeted against fatty acid biosynthesis, therefore it is unlikely that novel antibiotics of this type would be rendered inactive by known antibiotic resistance mechanisms. Moreover, this is a potentially broad-spectrum target. Therefore, FabH inhibitors would serve to meet this unmet need.

SUMMARY OF THE INVENTION

This invention comprises indole derivatives and pharmaceutical compositions containing these compounds and their use as FabH inhibitors that are useful as antibiotics for the treatment of Gram positive and Gram negative bacterial infections.

This invention further constitutes a method for treatment of a Gram negative or Gram positive bacterial infection in an animal, including humans, which comprises administering to an animal in need thereof, an effective amount of a compound of this invention.

DETAILED DESCRIPTION OF THE INVENTION

The compounds of this invention are represented by Formula (I):

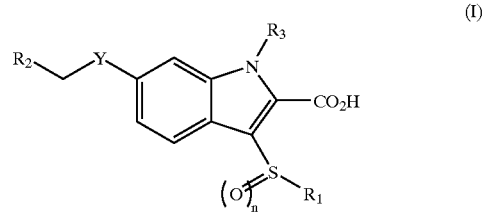

wherein:
  $R_1$ is selected from the group consisting of aryl, substituted aryl, heteroaryl, $C_{1-10}$ alkyl, cycloalkyl, arylalkyl, heteroarylalkyl and heterocyclicalkyl;
  $R_2$ is selected from the group consisting of aryl, substituted aryl, and heteroaryl;
  $R_3$ is selected from the group consisting of H, lower alkyl, CHO, and $COR_4$;
  $R_4$ is selected from the group consisting of aryl, substituted aryl, heteroaryl, and $C_{1-10}$ alkyl;
  n is an integer selected from the group consisting of 0, 1, and 2; and
  Y is selected from the group consisting of $CH_2$, $NR_3$, O, and S;
or a pharmaceutically acceptable salt thereof.

Also included in the invention are pharmaceutically acceptable salt complexes.

As used herein, "$C_{1-10}$ alkyl" or "alkyl" means both straight and branched chain rings of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic rings, preferably of 3 to 8 carbons, including but not limited to cyclopropyl, cyclopentyl, cyclohexyl, and the like.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

As used herein, "aryl" means phenyl and naphthyl;

As used herein, "heteroaryl" means a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

As used herein, preferred aryl substituents include halo, including chloro, fluoro, bromo and iodo, in any combination.

As used herein, "lower alkyl" means $C_{1-4}$ alkyl.

The compounds of this invention may contain one or more asymmetric carbon atoms and may exist in racemic and optically active forms. All of these compounds and diastereomers are contemplated to be within the scope of the present invention.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Preferred compounds of the present invention include:

6-(2,6-Dichlorobenzyloxy)-3-(phenylthio)indole-2-carboxylic acid; and 6-(2,6-Dichlorobenzyloxy)-3-(phenylsulfonyl)indole-2-carboxylic acid.

Compounds of the Formula (I) wherein $R_1$ is phenyl, $R_2$ is 2,6-dichlorophenyl, $R_3$ is H, and Y is O were prepared by the method described in Scheme 1.

Scheme 1

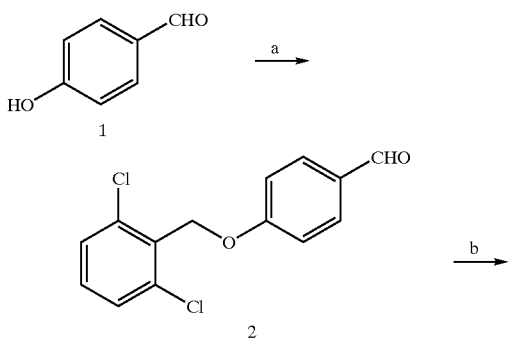

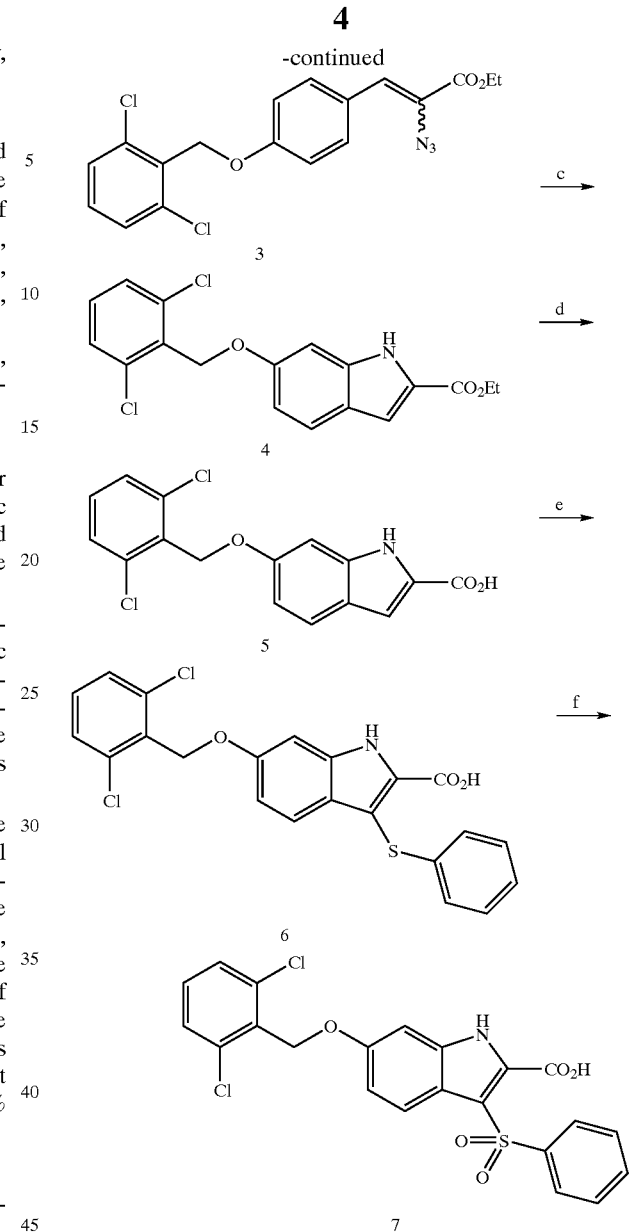

a) 2,6-Dichlorobenzyl Bromide, NaH, DMF; b) $N_3CH_2CO_2Et$, NaOEt, EtOH, −10° C.; c) 125° C., Xylene, 4 h; d) 1N NaOH, THF—MeOH, 50° C.; e) NaH, $Ph_2S_2$, DMF, 25→55° C.; f) 1) mCPBA, $CH_2Cl_2$.

4-Hydroxybenzaldehyde (1, Scheme 1) was reacted with 2,6-dichlorobenzyl bromide in the presence of NaH to form the ether 2. This aldehyde was then condensed with ethyl 2-azidoacetate to provide intermediate 3 which was then heated in xylene to yield the indole 4. Conversion of the ethyl ester 4 to the carboxylic acid 5 was accomplished by standard base hydrolysis with NaOH. Acid 5 was converted into the dianion using NaH followed by reaction with phenyldisulfide producing the desired phenylsulfide 6 (Example 1). Sulfone 7 (Example 2) was prepared from 6 via oxidation with a peracid; in this example m-chloroperoxybenzoic acid was used.

SYNTHETIC EXAMPLES

The invention will now be described by reference to the following examples which are merely illustrative and are not to be construed as a limitation of the scope of the present invention. All temperatures are given in degrees centigrade, and all solvents are highest available purity unless otherwise indicated.

Example 1

Preparation of 6-(2,6-Dichlorobenzyloxy)-3-(phenylthio)indole-2-carboxylic Acid a) 4-(2,6-Dichlorobenzyloxy)benzaldehyde To a solution of 4-hydroxybenzaldehyde (3.59 g, 24.39 mmol) and 2,6-dichlorobenzyl bromide (7.05 g, 29.39 mmol) in dimethylformamide (20 mL) at 0° C. was added 60% sodium hydride (1.176 g, 29.39 mmol). After stirring at ambient temperature for 16 h, the reaction was partitioned between ethyl acetate and water. The organic layer was washed with aqueous sodium chloride and dried (MgSO$_4$). Purification by flash column chromatography (silica gel, hexane/ethyl acetate) yielded an off-white solid (7.38 g, 89%). MS(ES) m/e 281.0 [M+H]$^+$.

b) Ethyl 2-Azido-3-[4-(2,6-dichlorobenzyloxy)phenyl]propenoate

Sodium (0.373 g, 0.016 g atom) was dissolved in absolute ethanol (12 mL). To this, a solution of the compound of Example 1a (1.0 g, 3.5 mmol) in ethanol (10 mL) was added followed by the dropwise addition of ethyl azidoacetate (1.80 g, 14.0 mmol) at −10° C. The reaction was stirred at −10° C. until tlc indicated that the aldehyde was consumed. After warming to ambient temperature, the reaction was quenched with ice water (50 mL) and extracted with ether. The organic layer was washed with aqueous sodium chloride and dried (MgSO$_4$). Purification by flash column chromatography (silica gel, hexane/ethyl acetate) yielded a yellow solid (658 mg, 48%). MS(ES) m/e 464.7 [M+H+DMF]$^+$.

c) Ethyl 6-(2,6-Dichlorobenzyloxy)indole-2-carboxylate

A solution of the compound of Example 1b (658 mg, 1.67 mmol) in xylene (20 mL) was heated at 125° C. for 4 h. The solvent was removed under reduced pressure and the crude product was purified by flash column chromatography (silica gel, hexanelethyl acetate) to yield a pale yellow solid (306 mg, 50%). MS(ES) m/e 346.9 [M−2H]$^-$.

d) 6-(2,6-Dichlorobenzyloxy)indole-2-carboxylic Acid

To a solution of the compound of Example 1c (306 mg, 0.84 mmol) in 1:2 methanol: tetrahydrofuran (6 mL) was added 1N aqueous sodium hydroxide (0.92 mL). The reaction was heated at 50° C. for 2 h. The solvents were removed under reduced pressure and the residue was partitioned between dilute hydrochloric acid and ethyl acetate. The organic layer was dried (MgSO$_4$) and evaporated to give an off-white solid. (194.4 mg, 69%). $^1$H NMR (400 MHz, CDCl$_3$) δ 10.02 (br s, 1H), 7.54 (d, J=8.8 Hz, 1H), 7.36 (m, 2H), 7.25 (d, J=8.5 Hz, 1H), 7.16 (s, 1H), 7.07 (s, 1H), 6.85 (dd, J=6.7, 2.2 Hz), 5.30 (s, 2H).

e) 6-(2,6-Dichlorobenzyloxy)-3-(phenylthio)indole-2-carboxylic Acid

To a solution of 60% sodium hydride (64.8 mg, 1.73 mmol) in dimethylformamide (1.0 mL) was added a solution of the compound of Example 1d (194 mg, 0.58 mmol) in dimethylformamide (0.5 mL). The reaction was stirred at ambient temperature until the evolution of H$_2$ ceased. A solution of phenyldisulfide (129.7 mg, 0.64 mmol) in dimethylformamide (1.0 mL) was added, followed by heating at 55° C. for 30 h. The cooled reaction was poured into water, acidified with dilute hydrochloric acid and extracted with ethyl acetate. The organic layer was washed with aqueous sodium chloride and dried (MgSO$_4$). Trituration with acetonitrile yielded a tan solid (63 mg, 24%). MS(ES) m/e 441.8 [M−H]$^-$.

Example 2

Preparation of 6-(2,6-Dichlorobenzvloxy)-3-(phenylsulfonyl)indole-2-carboxylic Acid To a solution of the phenylsulfide of Example 1e (55 mg, 0.12 mmol) in methylene chloride (1.0 mL) was added 80% 3-chloroperoxybenozic acid (57 mg, 0.26 mmol). The reaction was stirred at ambient temperature for 16 h. The solution was concentrated under reduced pressure and the crude product was converted to the sodium salt with aqueous sodium bicarbonate. Purification by reversed phase low pressure LC (ODS, step gradient, 20–90% methanol/water), followed by conversion to the carboxylic acid with dilute hydrochloric acid and subsequent trituration with acetonitrile yielded a white powder (17 mg, 29%). MS(ES) m/e 473.8 [M−H]$^-$.

Example 3

Preparation of 6-(2,6-Dichlorobenzyloxy)-3-(phenylsulfinyl)indole-2-carboxylic Acid To a solution of the phenylsulfide of Example 1e (57.2 mg, 0.13 mmol) in methylene chloride (1.0 ml) was added 80% 3-chloroperoxybenzoic acid (30.1 mg, 0.14 mmol). The reaction was stirred at ambient temperature for 16 h. The solution was concentrated under reduced pressure and the crude product was converted to the sodium salt with aqueous sodium bicarbonate. Purification by reversed phase low pressure LC (ODS, step gradient, 20–90% methanol/water), followed by lyopholization yielded a white powder (34.6 mg, 58 %). MS(ES) m/e 460.0 [M+H]$^+$, 457.99 [M−H]$^-$.

Biological Assay:

FabH was assayed in a coupled format using his-tagged S.aureus FabD, and acyl carrier protein (ACP) purchased from Sigma. Lyophilized ACP was reduced using β-mercaptoethanol in phosphate buffer. Malonyl-CoA, and FabD were added to the reduced ACP, thus generating malonyl-ACP. After the FabD reaction reached equilibrium, [$^{14}$C] acetyl-CoA and inhibitors were added, and the reaction started by the addition of FabH. TCA precipitation and filtration was used to separate [$^{14}$C] acetyl-CoA substrate from [$^{14}$C] acetoacetyl-ACP product.

Secondary and tertiary screens of suitable reproducibility, sensitivity, throughput and analytical power to progress primary screen hits are characterized, validated and in current use. Compounds are evaluated against purified mammalian fatty acid biosynthetic enzymes, E. coli FabH, FabB and a human lung cell cytotoxicity assay. In addition, whole-cell antibacterial activity is determined against a range of clinically relevant wild type and efflux impaired bacteria using standard and novel fluorescence based technologies. The FabH assay has been thoroughly characterized kinetically and a reaction mechanism proposed. Detailed studies have generated novel data about mechanism of inhibition by tool compounds, including thiolactomycin. Screens in use are of direct relevance to the therapeutic goal—eradication of bacteria from sites of infection ('cure'). Several state-of-the-art animal models of bacterial infection are available, meaningful and in current use in this and numerous other studies at SB. Extensive prior experience with known antibacterials confirm that bacterial kill in vitro and in animal models is an excellent indicator of bacterial kill in vivo and cure of infection.

The present invention also provides a pharmaceutical composition, which comprises a compound of formula (I) or a pharmaceutically acceptable salt or in vivo hydrolysable ester thereof, and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the compound of Formula (I) Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 1 to 140 mg/kg of body weight, depending on the route and frequency of administration. No unacceptable toxicological effects are expected when a compound of formula (I a) or a pharmaceutically acceptable salt or in vivo hydrolysable ester thereof is administered in the above-mentioned dosage range.

Inhibitors of β-ketoacyl-ACP Synthase (FabH) can be administered by injection in solutions either intravenously, intramuscularly, intraperitoneally, or orally. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the β-ketoacyl-ACP Synthase (FabH) inhibitor.

The compound of formula (I) may be the sole therapeutic agent in the compositions of the invention or a combination with other antibiotics or compounds which enhance the antibacterial activity of a compound of formula (I) may be employed.

The antibiotic compounds of the present invention are active against a wide range of organisms including both Gram-negative organisms such as *Escherichia coli* and *Klebsiella pneumoniae* and Gram-positive organisms such as *Staphylococcus aureus, Streptococcus pneumoniae, Enterococcus faecalis* and *Enterococcus faecium*, including isolates resistant to existing antibiotics.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating bacterial infections by administering to a patient in need thereof an effective amount of a compound of Formula (I):

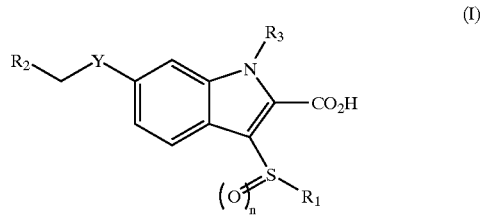

wherein:

$R_1$ is selected from the group consisting of aryl, substituted aryl, heteroaryl, $C_{1-10}$ alkyl, cycloalkyl, arylalkyl, heteroarylalkyl and heterocyclicalkyl;

$R_2$ is selected from the group consisting of aryl, substituted aryl, and heteroaryl;

$R_3$ is selected from the group consisting of H, lower alkyl, CHO, and $COR_4$;

$R_4$ is selected from the group consisting of aryl, substituted aryl, heteroaryl, and $C_{1-10}$ alkyl;

n is an integer selected from the group consisting of 0, 1, and 2; and

Y is selected from the group consisting of $CH_2$, $NR_3$, O, and S; or a pharmaceutically acceptable salt thereof.

2. A method of treatment according to claim 1 wherein the compound of Formula (I) is SB418011, 6-(2,6-Dichlorobenzyloxy)-3-(phenylthio) indole-2-carboxylic acid.

3. A method of treatment according to claim 1 wherein the compound of Formula (I) is 6-(2,6-Dichlorobenzyloxy)-3-(phenylsulfonyl) indole-2-carboxylic acid.

* * * * *